United States Patent
Klymchenko et al.

(10) Patent No.: US 11,549,886 B2
(45) Date of Patent: Jan. 10, 2023

(54) DYE-LOADED FLUORESCENT POLYMERIC NANOPARTICLES AS NANO-ANTENNA

(71) Applicants: UNIVERSITE DE STRASBOURG, Strasbourg (FR); CENTRE NATIONAL DE LA RECHERCHE SCIENTIFIQUE, Paris (FR)

(72) Inventors: Andrey Klymchenko, Illkirch (FR); Kateryna Trofymchuk, Munich (DE); Andreas Reisch, Colmar (FR); Bohdan Andreiuk, Boston, MA (US)

(73) Assignees: UNIVERSITE DE STRASBOURG, Strasbourg (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 404 days.

(21) Appl. No.: 16/624,696

(22) PCT Filed: Jun. 21, 2018

(86) PCT No.: PCT/EP2018/066545
§ 371 (c)(1),
(2) Date: Dec. 19, 2019

(87) PCT Pub. No.: WO2018/234431
PCT Pub. Date: Dec. 27, 2018

(65) Prior Publication Data
US 2020/0110032 A1    Apr. 9, 2020

(30) Foreign Application Priority Data

Jun. 21, 2017 (EP) .................................. 17305763

(51) Int. Cl.
*G01N 21/64* (2006.01)
*C09B 11/24* (2006.01)
*C09K 11/02* (2006.01)
*C09K 11/06* (2006.01)

(52) U.S. Cl.
CPC .......... *G01N 21/6428* (2013.01); *C09B 11/24* (2013.01); *C09K 11/02* (2013.01); *C09K 11/06* (2013.01); *C09K 2211/1018* (2013.01); *G01N 2021/6439* (2013.01)

(58) Field of Classification Search
None
See application file for complete search history.

(56) References Cited

FOREIGN PATENT DOCUMENTS

EP    2811298 A1    12/2014

OTHER PUBLICATIONS

European Search Report from European Patent Application No. 17305763.9, dated Dec. 21, 2017.
International Search Report from corresponding International Patent Application No. PCT/EP2018/066545, dated Sep. 13, 2018.
Acuna et al., "Fluorescence Enhancement at Docking Sites of DNA-Directed Self-Assembled Nanoantennas", Science (2012), 338(6106), pp. 506-510.

(Continued)

*Primary Examiner* — Edwin C Gunberg
(74) *Attorney, Agent, or Firm* — Greer, Burns & Crain, Ltd

(57) ABSTRACT

Dye-loaded fluorescent polymeric nanoparticles working as light-harvesting nano-antenna, which efficiently transfer the excitation energy to acceptor dyes and, therefore, amplifies emission of the latter are provided.

16 Claims, 7 Drawing Sheets

(56) References Cited

OTHER PUBLICATIONS

De Torres et al., "Plasmonic Nanoantennas Enable Forbidden Forster Dipole-Dipole Energy Transfer and Enhance the FRET Efficiency", Nano Letters (2016), 16(10), pp. 6222-6230.

Holzmeister et al., "Breaking the Concentration Limit of Optical Single-Molecule Detection", Chemical Society Reviews (2014), 43(4), pp. 1014-1028.

Levitus, Marcia, "Handbook of Fluorescence Spectroscopy and Imaging", Angewandte Chemie International Edition (2011), 50(39), pp. 9017-9018.

Peng et al., "Biological Applications of Supramolecular Assemblies Designed for Excitation Energy Transfer", Chemical Reviews (2015), 115(15), pp. 7502-7542.

Reisch et al. "Collective Fluorescence Switching of Counterion-Assembled Dyes in Polymer Nanoparticles", Nature Communications (2014), 5(4089), pp. 1-9.

Shulov et al., "Fluorinated Counterion-Enhanced Emission of Rhodamine Aggregates: Ultrabright Nanoparticles for Bioimaging and Light-Harvesting", Nanoscale (2015), 7(), pp. 18198-18210.

Wagh et al., "Development of Biocompatible Polymeric Nanoparticles for in Vivo NIR and FRET Imaging", Bioconjugate Chemistry (2012), 23(5), pp. 981-992.

Wagh et al., "Polymeric Nanoparticles with Sequential and Multiple FRET Cascade Mechanisms for Multicolor and Multiplexed Imaging", Small (2013), 9(12), pp. 2129-2139.

Wagh et al., "Polymeric Nanoparticles with Sequential and Multiple FRET Cascade Mechanisms for Multicolor and Multiplexed Imaging", Supporting Information, pp. 1-11.

Zou et al., "Noninvasive Fluorescence Resonance Energy Transfer Imaging of in Vivo Premature Drug Release from Polymeric Nanoparticles", Molecular Pharmaceutics (2013), 10(11), pp. 4185-4194.

Figure 2.
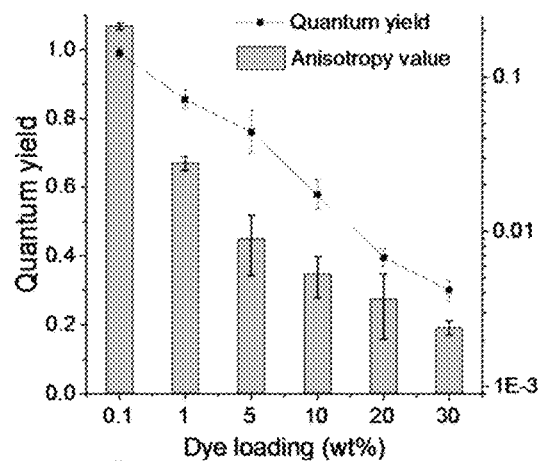
FIG. 2A
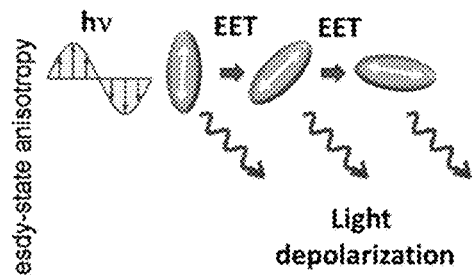
FIG. 2B
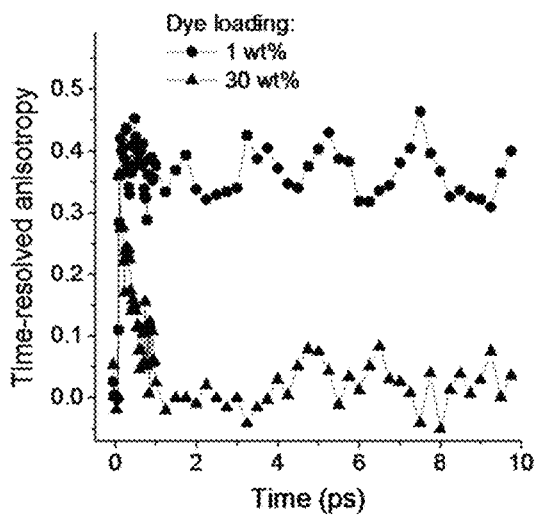
FIG. 2C
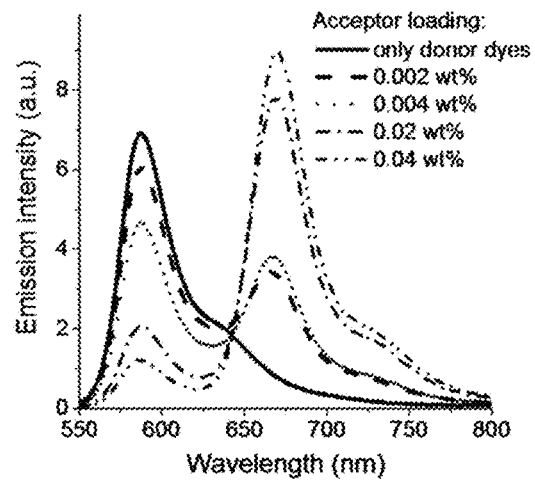
FIG. 2D
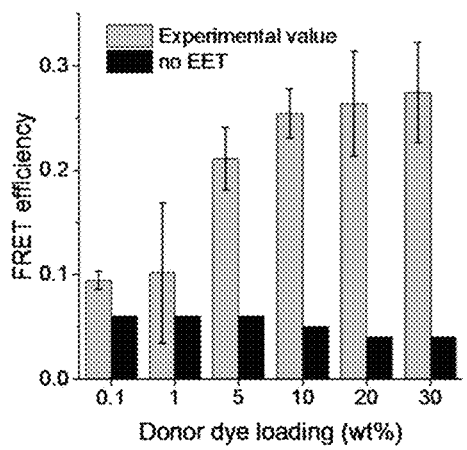
FIG. 2E
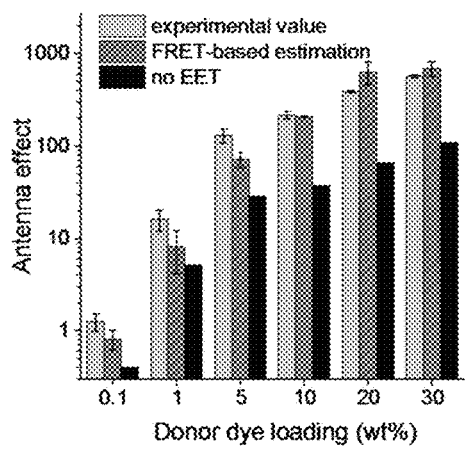
FIG. 2F Figure 5.
FIG. 5A
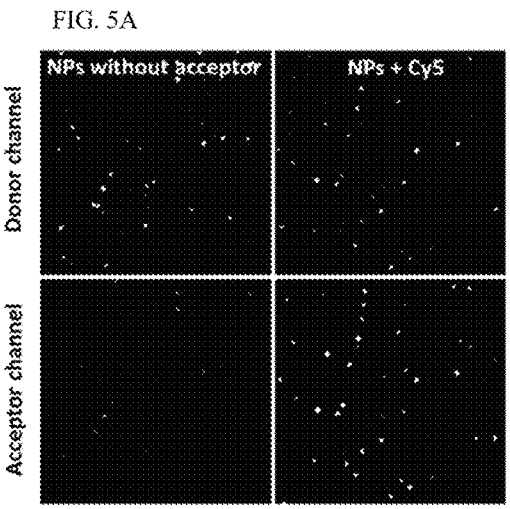
FIG. 5B
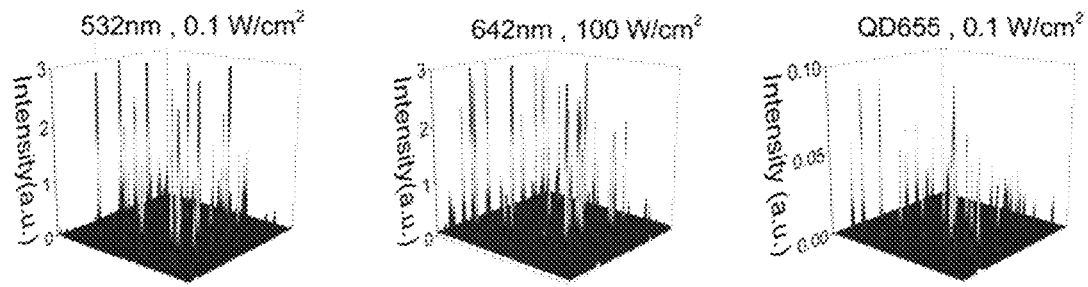
FIG. 5C
FIG. 5D
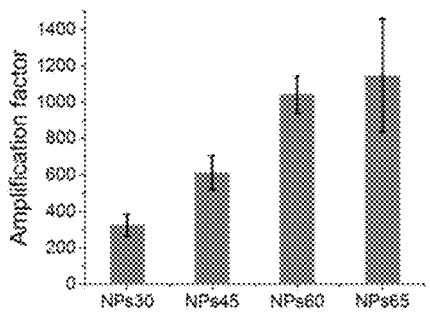
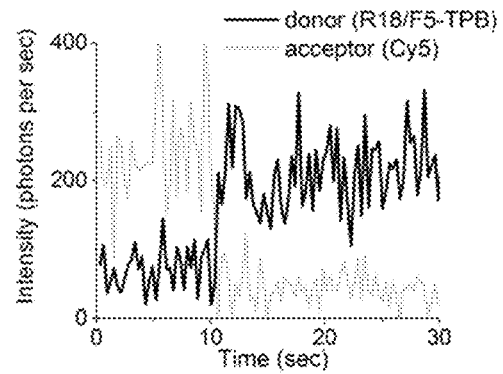

Figure 5 (Cont'd).
FIG. 5E
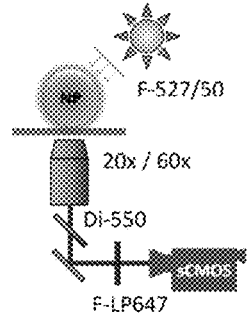
FIG. 5F
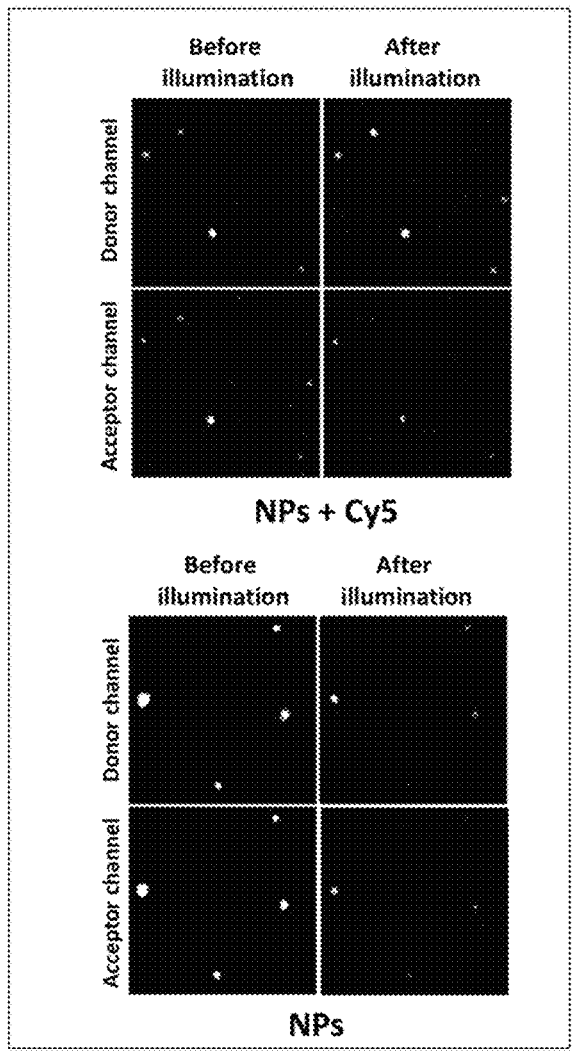
FIG. 5G
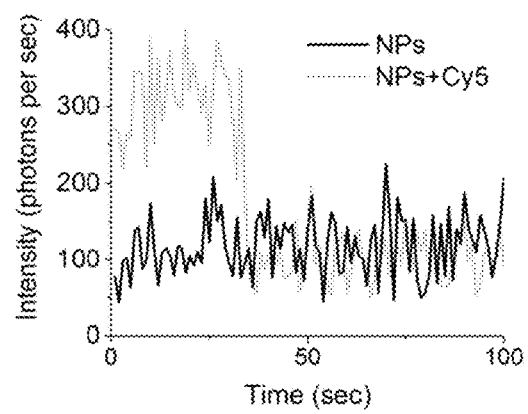

DYE-LOADED FLUORESCENT POLYMERIC NANOPARTICLES AS NANO-ANTENNA

BACKGROUND

The present invention concerns dye-loaded fluorescent polymeric nanoparticles working as nano-antenna.

Detection of single fluorescent molecules requires a dedicated microscopy setup with strong excitation power ranging between 100 and up to 5000 W/cm² because the brightness of fluorescent dyes is limited (Holzmeister, P.; Acuna, G. P.; Grohmann, D.; Tinnefeld, P. *Chemical Society Reviews* 2014, 43, (4), 1014-1028.). However, the use of strong excitation power would increase photo-damage and the background related to auto-fluorescence, and need special microscopy setups and powerful light source. The use of much lower excitation power would not only decrease photo-damage and auto-fluorescence background, but also enable utilization of inexpensive light sources important for high-throughput screening and diagnostics assays.

For instance, fluorescent nanoparticles (NPs), that are many-fold brighter than single dyes, can be detected even using a smartphone-based device. Till now, a single fluorescent molecule detection under ambient light conditions was impossible. The typical light power of sunlight at the surface of the earth at a bandwidth of 10 nm in a visible range is 1-5 mW/cm², which is similar to the illumination power used in fluorimeters or plate readers. This power is $10^4$-$10^6$ times lower than those typically used in single molecule microscopy.

One of recent developed method suggested metallic nano-structures, so-called plasmonic nano-antennas, which can amplify the excitation and emission of single molecules (Novotny, L.; van Hulst, N. *Nat. Photonics* 2011, 5, (2), 83-90.). In this case, the amplification is achieved due to surface plasmon effects, which requires precise control of antenna geometry and the distance from the emitter to the metal surface. Thus, between two gold NPs, an amplification of up to 100-fold could be achieved (Acuna, G. P.; Möller, F. M.; Holzmeister, P.; Beater, S.; Lalkens, B.; Tinnefeld, P. *Science* 2012, 338, (6106), 506-510.). However, to detect single molecule under ambient light power, it is needed to achieve at least 1000-fold amplification of the signal coming from a high performance non-quenched fluorophore, such as cyanine 5 or Alexa567.

Another method concerns the use of a light-harvesting concept, where multiple donors due to high absorptivity can efficiently collect light energy and then deliver it to a single acceptor through a Förster Resonance Energy transfer (FRET) mechanism. This is particularly efficient when the excitation energy can rapidly migrate within the donors up to the energy acceptor. FRET systems that use conjugated polymers, dendrimers, multi-porphyrin arrays, micellar NPs, polymer NPs, dye assemblies, metal-organic frameworks, nucleic acids, etc, have been developed.

The values of antenna effect reported in the literature for FRET-based systems vary in the range of 3-100. So far the obtained amplification of the acceptor emission has never reached 1000 (Peng, H.-Q.; Niu, L.-Y.; Chen, Y.-Z.; Wu, L.-Z.; Tung, C.-H.; Yang, Q.-Z. *Chemical Reviews* 2015, 115, (15), 7502-7542.). The common reasons that limit the efficient light harvesting is self-quenching of donors at high local concentration and/or inefficient donor-donor coupling.

Recent work showed that encapsulation of multiple dyes inside polymer NPs using bulky counterions can minimize aggregation-caused dye self-quenching and produce fluorescence switching (blinking) of up to 500 dyes per particle (Reisch, A.; Didier, P.; Richert, L.; Oncul, S.; Arntz, Y.; Mely, Y.; Klymchenko, A. S. *Nat. Commun.* 2014, 5:4089). It was explained by coupling of encapsulated dyes due to exciton migration, so that a single dark species of the same dye could quench the whole dye ensemble. However, these nanoparticles produce only on/off fluorescence switching and cannot generate any antenna effect. This article neither teach the amplification of the acceptor emission for a different dye (e.g. cyanine), which serves as energy acceptor.

Shulov et al. (Shulov, I.; Oncul, S.; Reisch, A.; Arntz, Y.; Collot, M.; Mely, Y.; Klymchenko, A. S. *Nanoscale* 2015, 7, (43), 18198-18210) described fluorescent nanoparticles (NPs) of 10-20 nm in suspension. Said NPs contain rhodamine dyes as FRET energy donor which is assembled with the help of fluorinated counterion and a cyanine-derivative (C2-cy5) as FRET energy acceptor. However, in this work, the nanoparticles used were composed exclusively of dyes without polymer matrix. Moreover, these NPs could not produce enough high antenna effect to make energy acceptor be excited under ambient light conditions, since these NPs can only contain no more than 400 rhodamine dyes.

In fact, the combination of components giving a giant light harvesting process that enable detection of single molecules in ambient light conditions has never been achieved before with any optical material.

Consequently, it is necessary to develop new dye-loaded polymer nanoparticles which have a higher antenna effect and can be excited in condition similar to ambient light.

SUMMARY

One subject-matter of the present invention concerns a dye-loaded fluorescent polymeric nanoparticle as nano-antenna, said nanoparticle comprising:
a) a polymer chosen from:
   a polymethacrylate or its derivative,
   a polystyrene or its derivative,
   an aliphatic polyester or its derivative, or
   a copolymer of aforementioned polymers with polyethylene glycol or with charged monomers,
b) an energy donor, which content is from 5 to 50% by weight of the polymer, preferably from 10 to 30% by weight of the polymer,
c) an energy acceptor, which content is from 0.001 to 0.04% by weight of the polymer, preferably from 0.002 to 0.02% by weight of the polymer;
said polymer forming a matrix in which from 1000 to 50000 of said energy donor molecules are encapsulated per nanoparticle,
wherein the energy donor is a salt of a donor dye with bulky fluorinated anions, said donor dye being chosen from:
   i) a rhodamine derivative represented by formula (I)

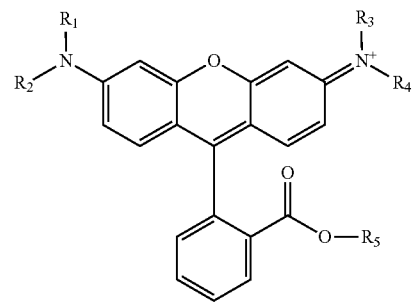

in which:
R₁, R₂, R₃ and R₄ are identical or different and each represent a hydrogen or a ($C_1$-$C_8$) alkyl group,
R₅ is a ($C_1$-$C_{24}$) alkyl, or
ii) a cyanine derivative represented by formula (II)

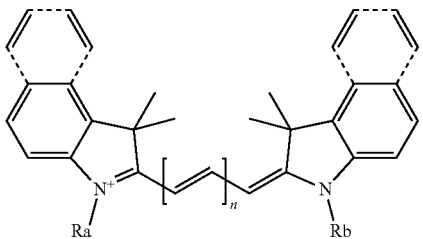

in which:
n is a integer chosen from 1, 2 or 3;
Ra and Rb are identical or different and each represent a ($C_1$-$C_{24}$) alkyl group;
and wherein the energy acceptor is a salt of another cyanine derivative of formula (II) defined above with a counterion, said energy donor and said energy acceptor being different.

The term "dye-loaded fluorescent polymeric nanoparticle" is meant to a polymeric nanoparticle wherein fluorescent dyes are loaded in the matrix or on the surface of the nanoparticle.

The term "nano-antenna" is meant here to a nanoparticle that can transfer effectively excitation energy of light from a large number of energy donors to few energy acceptors within the nanoparticle and, therefore, can amplify the emission of the acceptor.

It is observed that the NPs of the present invention generate unprecedented 1000-fold amplification (antenna effect) of a single cyanine 5 derivative (DiD) acceptor emission when it is located inside the particles.

When a cyanine 5 derivative (Cy5-C2) is located at the particle surface, the antenna effect of the NP is still more than 200 (i.e. >200-fold amplification of emission of a single cyanine 5 derivative, Cy5-C2), which have never been reached before by a known NP having energy acceptor on the particle surface.

This result enables for the first time the observation of single molecules under ambient light conditions, that is to say with an excitation of the power density of 1 mW/cm², which is $10^4$-$10^6$ fold lower than typically used in single molecule measurements. The unique efficiency of nanoparticles (NPs) of the present invention relies on two key factors. The first one is the high quantum yield of 1000 to 50000 energy donors encapsulated within the polymer, which ensures that a large part of the excitation energy is delivered to the acceptor with minimal energy loss. The second factor is the exceptionally fast excitation energy migration within the encapsulated energy donors on the time scale less than 30 fs, which ensures efficient delivery of the excitation energy to single accepters from thousands of donors through distances beyond the Förster radius.

The term "antenna effect" is referred to amplification factor of the acceptor emission which is measured from the excitation spectra, recorded at the emission wavelength of the acceptor, and is expressed as the ratio of the maximal excitation intensity of the donor to that of the acceptor with appropriate correction.

Polymer

The polymer contained in the nanoparticles of the invention provides a physical structure support and a matrix in which the energy donors and eventually the energy acceptors are encapsulated.

The term "polymethacrylate" as used herein, means a polymer of salt or ester of polymethacrylic acid, which monomer can be represented by the formula —[(ROCO)C(Me)CH₂]—, wherein R is a hydrogen, an ($C_1$-$C_5$)alkyl, a cationic or a anionic group. Examples of polymethacrylates include, but are not limited to, poly(methyl methacrylate), poly(ethyl methacrylate), poly(butyl methacrylate).

According to the invention, a derivative of polymethacrylate means a polymethacrylate bearing one or more substitutions on its side chain. Said substitution can be an aliphatic group, hydrogen, aromatic group, an anionic or cationic group. Examples of derivative of polymethacrylate are poly(methyl methacrylate-co-methacrylic acid) (PMMA-MA), poly(methyl methacrylate-co-2-methacrylamidoethane-sulfonic acid) (PMMA-SO3).

The term "polystyrene" as used herein, means an aromatic polymer synthetized from the monomer which is styrene, or a derivative of styrene.

According to the invention, a derivative of polystyrene means a polystyrene bearing one or more substitutions on its side chain. Said substitution can be an anion, such as a sulfonate, phosphate, phosphonate, phosphoryl, and carboxyl, or a cation, such as a quaternary ammonium, or a tertiary ammonium. Examples of derivative of polystyrene can be polystyrene sulfonates, polystyrene phosphonate, carboxypolystyrene.

The term "aliphatic polyester" as used herein, means a group of aliphatic polymers containing ester functional group in the repeat units of main chain. Examples of aliphatic polyesters can be cited as, but are not limited to, polycaprolactone (PCL), poly(lactic acid) (PLA), poly(glycolic acid) (PGA), poly(lactide co-glycolide) (PLGA).

The polymer used in the present invention can also be a copolymer of one of the aforementioned polymer with polyethylene glycol or with charged monomer, that is to say a polymer obtained by copolymerisation of a monomer of an aforementioned polymer with the monomer of ethylene glycol, or a charged monomer.

The term "charged monomer" is referred to an organic molecule used for polymerization, which bears charged group, such as quaternary ammonium, carboxylate or sulfonate.

In a particular embodiment of the present invention, the polymer comprised in the nanoparticles is chosen from polycaprolactone, poly(lactic acid), poly(glycolic acid), poly(Lactide-co-Glycolide), poly(methyl methacrylate), poly(methyl methacrylate-co-methacrylic acid), and poly(Lactide-co-Glycolide-co-PEG).

In a preferred embodiment of the present invention, the polymer is chosen from polycaprolactone, poly(methyl methacrylate), poly(methyl methacrylate-co-methacrylic acid), and poly (Lactide-co-Glycolide-co-PEG).

More preferably, the polymer is poly(methyl methacrylate-co-methacrylic acid) (PMMA-MA) having molecular weight in the range from 10000 to 300000 and containing from 1 to 5% by weight of methacrylic acid.

Energy Donor

In the nanoparticles of the present invention, the energy donor is encapsulated in the matrix of the polymer.

The term "encapsulated" is meant to enclose an energy donor inside the matrix of polymer.

The content of energy donor in a nanoparticle of the invention is from 5 to 50% by weight of the polymer, preferably from 10 to 30% by weight of the polymer.

In a particular embodiment, content of energy donor in a nanoparticle of the present invention is from 50 to 700 mmol/kg, in particular from 50 to 300 mmol/kg, more in particular 150-200 mmol/kg with respect to the total mass of the nanoparticles.

In said particular embodiment, the conversion formula is as follows:

$$M(\text{dye salt}) = W(\text{dye salt}) * 1000000 / [Mr(\text{dye salt}) * (100 + \text{wt \%})]$$

where

M(dye salt) is molar concentration with respect to total weight of particle (mmol/kg)

W(dye salt) is mass concentration (wt %) with respect to polymer of particle

Mr(dye salt) is molecular weight of dye salt (g/mol)

This high content ensures a huge number of energy donor encapsulated in the nanoparticle of the invention. According to the present invention, the number of energy donor per nanoparticle is from 1000 to 50000, particularly from 2000 to 10000.

The diameter of the nanoparticles of the present invention is varied from 10 nm to 150 nm, preferably in the range from 20 nm to 140 nm, from 30 nm to 130 nm, more preferably in the range from 25 to 70 nm, or more preferably in the range from 90 nm to 110 nm. Nanoparticle's diameter can be measured according to a conventional method by electron microscopy.

In an embodiment of the present invention, the energy donor is a salt of a rhodamine of formula (I) with bulky fluorinated anions.

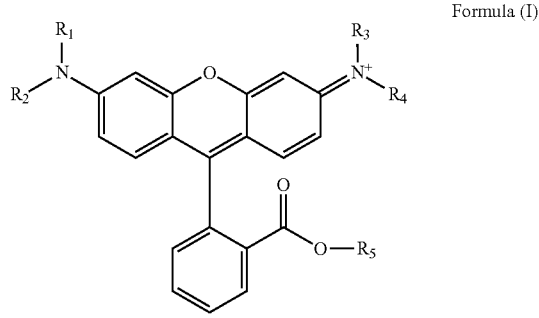

Formula (I)

In the above formula (I):
$R_1$, $R_2$, $R_3$ and $R_4$ are identical or different and each represent a hydrogen or a ($C_1$-$C_8$) alkyl group,
$R_5$ is a ($C_1$-$C_{24}$) alkyl.

The term "($C_1$-$C_8$) alkyl group" as used herein, means a saturated straight or branched hydrocarbon chain containing from 1 to 8 carbons. Representative examples of ($C_1$-$C_8$) alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl.

The term "($C_1$-$C_{24}$) alkyl group" is referred to a saturated straight or branched hydrocarbon chain containing from 1 to 24 carbons. Examples of ($C_1$-$C_{24}$) alkyl group can be, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-un- decyl, n-docenyl, n-tridecyl, n-tetradecyl, n-pentadecyl, n-hexadecyl, n-heptadecyl, n-octadecyl, n-nonadecyl, n-icosyl, n-henicosyl, n-docosyl, n-tricosyl, n-tetracosyl.

In a preferred embodiment, the rhodamine used in the present invention is rhodamine B octadecyl ester of formula (Ia) hereafter.

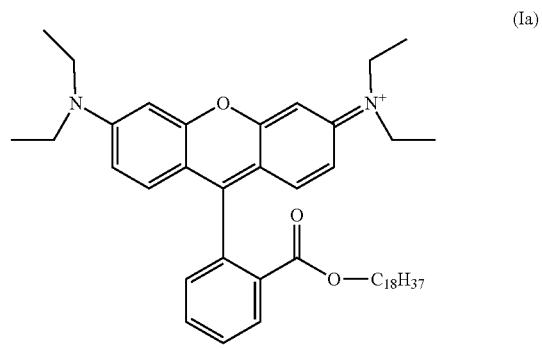

Formula (Ia)

In another embodiment of the present invention, the energy donor is a salt of a cyanine derivative of formula (II) with bulky fluorinated anions.

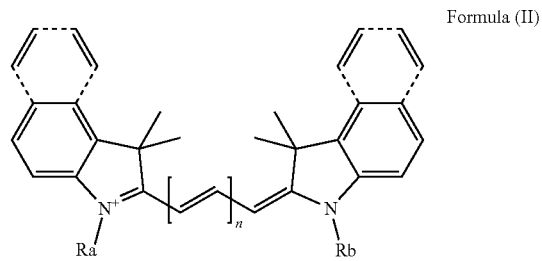

Formula (II)

The above formula (II) is meant to be a compound of formula (IIa) or a compound of formula (IIb)

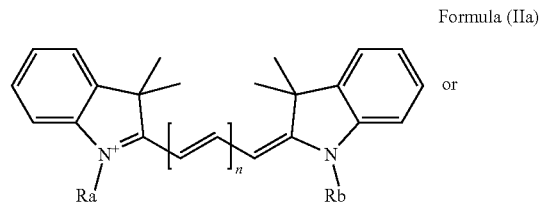

Formula (IIa) or

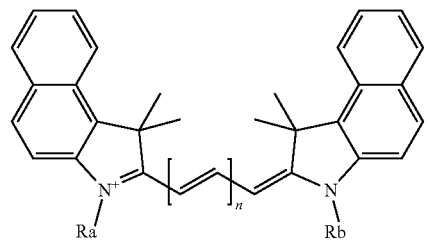

Formula (IIb)

wherein:
n is a integer chosen from 1, 2 or 3;
Ra and Rb are identical or different and represent each a ($C_1$-$C_{24}$) alkyl group.

A compound of formula (IIa), wherein n=1, corresponds to a Cy3 dye. An example of Cy3 dye is 1,1'-Dioctadecyl-3,3,3',3'-Tetramethylindocarbocyanine (DiI).

A compound of formula (IIa), wherein n=2, corresponds to a Cy5 dye. An example of Cy5 dye is 1,1'-Dioctadecyl-3,3,3',3'-Tetramethylindodicarbocyanine (DiD).

A compound of formula (IIa), wherein n=3, corresponds to a Cy7 dye. An example of Cy7 dye is 1,1'-Dioctadecyl-3,3,3',3'-Tetramethylindotricarbocyanine (DiR).

A compound of formula (IIb), wherein n=1, corresponds to a Cy3.5 dye. An example of Cy3.5 dye is 1,1'-Dioctadecyl-3,3,3',3'-Tetramethylbenzindocarbocyanine.

A compound of formula (IIb), wherein n=2, corresponds to a Cy5.5 dye. 1,1'-Dioctadecyl-3,3,3',3'-Tetramethylbenzindodicarbocyanine is an example of Cy5.5.

A compound of formula (IIb), wherein n=3, corresponds to a Cy7.5 dye. 1,1'-Dioctadecyl-3,3,3',3'-Tetramethylbenzindotricarbocyanine is an example of Cy7.5.

In an energy donor, a rhodamine of formula (I) or a cyanine derivative of formula (II) respectively described above works as energy donor dye, which can be excited by an initial illumination source.

The term "bulky fluorinated anions" as used herein is a large organic anion bearing aromatic and/or aliphatic fluorinated residues. Said bulky fluorinated anions work not only as counterion in energy donor but also as a spacer between the donor dyes that, on one hand, prevents their aggregation and self-quenching and, on the other hand, brings the energy donor dyes in very close proximity to enable ultrafast diffusion of excitation energy with minimal loss.

According to a particular embodiment of the present invention, the bulky fluorinated anion is chosen from tetrakis(pentafluorophenyl)borate (F5-TPB), tetrakis[3,5-bis-(trifluoromethyl)phenyl]borate (F6-TPB), tetrakis[3,5-bis-(1,1,1,3,3,3-hexafluoro-2-methoxy-2-propyl)phenyl]borate (F12-TPB) and tetrakis[perfluoro-tert-butoxy]aluminate (F9-Al).

Energy Acceptor

In the nanoparticles of the present invention, the energy acceptor can either be encapsulated inside the matrix of the polymer or linked to the polymer by a covalent bond or adsorbed on the surface of polymer.

In a nanoparticle of the present invention, the content of the energy acceptor is from 0.001 to 0.04% by weight of the polymer, preferably from 0.002 to 0.02% by weight of the polymer.

According to the present invention, the ratio between energy acceptor and energy donor contained in a nanoparticle is from 1:1000 to 1:50000, preferable from 1:1000 to 1:10000.

Thanks to this ratio between energy acceptor and energy donor, a nanoparticle of the present invention harvests energy from a huge number of energy donors to a single energy acceptor and consequently amplifies the fluorescence emission of the energy acceptor.

According to the present invention, said energy acceptor is a salt of a cyanine derivative of formula (II) defined above with a counterion.

Said cyanine derivative works as an energy acceptor dye, which can be excited by the donor dyes of the same nanoparticle.

In an embodiment of the present invention, when the energy donor dye is a cyanine derivative of formula (II), the energy acceptor dye is another different cyanine derivative of formula (II). The rule to choose two compatible cyanine derivatives is that the emission spectrum of the donor dye should overlap the absorption spectrum of the acceptor dye.

According to the present invention, a counterion of the energy acceptor dye is an inorganic anion chosen from chloride, bromide, iodide, perchlorate, sulfonate, nitrate, tosylate, or an organic anion chosen from tetrakis(pentafluorophenyl)borate (F5-TPB), tetrakis[3,5-bis-(trifluoromethyl)phenyl]borate (F6-TPB), tetrakis[3,5-bis-(1,1,1,3,3,3-hexafluoro-2-methoxy-2-propyl)phenyl]borate (F12-TPB) and tetrakis[perfluoro-tert-butoxy]aluminate (F9-Al).

According to the present invention, the preferred energy donor is chosen from a salt of rhodamine B octadecyl ester, Cy3, Cy5, Cy3.5, or Cy5.5 with an above-mentioned bulky fluorinated anions.

The preferred energy acceptor is chosen from a salt of Cy5, Cy5.5, Cy7, Cy 7.5 with an above-mentioned anion.

More preferably, the energy donor is chosen from a salt of rhodamine B octadecyl ester, DiI, DiD, Cy3.5, or Cy5.5 with F5-TPB anion.

The preferred energy acceptor is chosen from a salt of DiD, Cy5.5, Cy7, or Cy7.5 with F5-TPB anion.

Preferable energy donor/acceptor couples formed by above mentioned energy donors and acceptors are given in the below table I:

TABLE I

| Donor/Acceptor |
| --- |
| rhodamine B octadecyl ester salt/DiD salt |
| rhodamine B octadecyl ester salt/Cy5.5 salt |
| DiI salt/DiD salt |
| DiI salt/Cy5.5 salt |
| DiI salt/Cy7 salt |
| DiD salt/Cy7 salt |
| Cy3.5 salt/Cy5.5 salt |
| Cy3.5 salt/Cy7.5 salt |
| Cy5.5 salt/Cy7.5 salt |

In a preferred embodiment, the nanoparticles of the present invention are poly(methyl methacrylate-co-methacrylic acid) based fluorescent nanoparticles, said nanoparticle comprising:
  a) from 5 to 50% by weight of the polymer, preferably from 10 to 30% by weight of the polymer of octadecyl-rhodamine B or DiI salt with bulky fluorinated anions as energy donor,
  b) from 0.001 to 0.04% by weight of the polymer, preferably from 0.002 to 0.02% by weight of the polymer, of cyanine 5 derivative DiD salt as energy acceptor,
the polymer nanoparticle encapsulating from 1000 to 50000 of said energy donor molecules.

In a more preferred embodiment, the nanoparticles of the present invention are poly(methyl methacrylate-co-methacrylic acid) based fluorescent nanoparticles, said nanoparticle comprising:
  a) from 5 to 50% by weight of the polymer, preferably from 10 to 30 by weight of the polymer of octadecyl-rhodamine B salt with tetrakis(pentafluorophenyl)borate (F5-TPB) as energy donor,
  b) from 0.001 to 0.04% by weight of the polymer, preferably from 0.002 to 0.02% by weight of the polymer, of cyanine 5 derivative DiD salt as energy acceptor;
  the polymer nanoparticle encapsulating from 1000 to 50000 of said energy donor molecules.

The fluorescent nanoparticles of the present invention can be excited by a power density from 1 to 1000 mW/cm$^2$, preferably 5-30 mW/cm², at 530 nm with up to 50 nm bandwidth. This excitation power density is similar to that under ambient light conditions and is 10 to 10000 fold lower than required in single fluorescent molecule measurements.

The nanoparticles of the present invention enable detection of single fluorescent molecule (FRET acceptor dye) using simple sCMOS-camera-based imaging setup under ambient sunlight-like conditions, which opens the ways to single molecule photography.

In a particular embodiment of the present invention, the surface of nanoparticles of the present invention is modified to increase the stabilization of the nanoparticles in biological media or for implementing specific interactions with biological targets.

The surface modification can be carried out through the adsorption of a polymeric or lipidic amphiphile bearing at least one polyethylene glycol chain or zwitterionic groups.

Examples of polymeric amphiphile can be cited are poloxamers, polysorbates, and 1,2-distearoyl-sn-glycero-3-phosphoethanolamine-Poly(ethylene glycol).

The term "zwitterionic group" as used herein, means a neutral group with both positive and negative electrical charge. Examples of zwitterionic groups include, but are not limited to, alkyl-dimethylammoniumpropane sulfonate.

The surface of said nanoparticle can also be covalently modified by polyethylene glycol or zwitterionic groups.

Another subject-matter of the present invention concerns a method for producing an aforementioned polymer-based fluorescent nanoparticle, with an energy acceptor and an energy donor encapsulated inside the nanoparticle.

Said method comprises the following steps:
(i) preparing a water-miscible solvent solution of a polymer as defined above, containing:
 a. from 0.001 to 0.04% by weight of the polymer, preferably from 0.004 to 0.02% by weight of the polymer of an energy acceptor;
 b. from 5 to 50% by weight of the polymer, preferably from 10 to 30% by weight of the polymer of an energy donor,
(ii) nanoprecipitating said water-miscible solvent solution of polymer in a basic, neutral or weakly acidic aqueous buffer to obtain said polymer-based fluorescent nanoparticles.

The water-miscible solvent can be, for example, acetonitrile, acetone, dioaxane, tetrahydrofurane, dimethylformamide.

The concentration of said polymer in said water-miscible solvent can be determined according to the nature and the solubility of said polymer in said solvent, for example, in the range from 0.1 to 20 mg/ml of solvent, preferable, 1.2 mg/ml of solvent.

The aqueous buffer can be any conventional basic, neutral or weakly acidic buffer, such as phosphate buffer. The concentration of said buffer can be determined according to the desired pH value. For example, when phosphate buffer is used, its concentration can be in the range from 1 to 50 mM; the pH of this buffer can be from 9.0 to 5.8. The pH value of said aqueous buffer determines the size of nanoparticles obtained after nanoprecipitation: lower pH leads to larger size of particles.

Another subject-matter of the present invention concerns a method for producing an aforementioned polymer-based fluorescent nanoparticle with an energy acceptor absorbed at the nanoparticle surface and an energy donor encapsulated inside the nanoparticle.

Said method comprises the following steps:
(i) preparing a water-miscible solvent solution of a polymer as defined above containing from 5 to 50% by weight of the polymer, preferably from 10 to 30% by weight of the polymer, of an energy donor,
(ii) nanoprecipitating said water-miscible solvent solution of polymer in a basic, neutral or weakly acidic aqueous buffer to obtain nanoparticles which encapsulate the energy donor.
(iii) adding a water-miscible solvent solution of acceptor to above aqueous buffer containing nanoparticles to a final concentration from 0.001 to 0.04% by weight of the polymer, preferably from 0.002 to 0.02% by weight of the polymer.

The concentration of the polymer in the water-miscible solvent solution of the polymer can be in the range from at 0.1-5 mg/ml, preferably, 1-2 mg/ml.

The aqueous buffer can be any conventional basic or weak acidic buffer, such as phosphate buffer. The aqueous buffer concentration can be in the range from 1 to 50 mM.

Thanks to giant light harvesting antenna effect, a polymer-based fluorescent nanoparticle of the present invention can be used as nano-antenna to amplify the fluorescence emission of a single energy acceptor dye. Therefore, the emission of the acceptor dye can be much brighter than that of classical dyes or nanoparticles excited at the same conditions. For example, single Cy5 energy acceptor inside a nano-antenna of the invention is 25-fold brighter than QD655 at 532 nm excitation.

The NPs of the invention can be used for in vitro or in vivo detecting non-labeled biomolecules, which can be targeted by the NPs of the invention. Particularly, the NPs of the invention can be used for detecting biomolecular markers of certain diseases.

The recognition between a biomolecule and a NP of the invention can be carried out, for example, through a ligand bound to the NP which can be recognized by the biomolecule through a domain of said biomolecule or a complementary ligand born by the biomolecule. Said ligand and its complementary ligand can be an antigen and an antibody, the biotin and the strepatvidine, two complementary DNA, a DNA or a peptide aptamer and its molecular target. Thus, the presence of said biomolecule in a sample can be indicated by appearance of a fluorescent signal in acceptor emission channel.

A nanoparticle of the invention bearing the energy acceptor on its surface can be used for detecting non-labeled biomolecules in "signal off" mode.

To obtain the response of the nanoparticles of the invention to the non-labeled biomolecule, this biomolecule after being recognized by the particle will displace the acceptor from the surface. In this case, the ligands born by the NPs are bound to the energy acceptor located on the surface of NPs. When said NPs interacts with biomolecules of interest through the ligands, the binding force between the biomolecule of interest and the ligand will remove the acceptor located at the NPs surface and thus will stop energy transfer from energy donors encapsulated in the NPs to the energy acceptor on the surface of NPs. Thus, the presence of biomolecules of interest will be detected by increase of energy donor emission and decrease of acceptor emission.

Due to amplification of brightness of single acceptor, the NPs of the invention can carry out single-molecule and single-particle tracking, which can be used for imaging single biomolecule in living cells. The NPs of the present invention can also be used in in vivo imaging. For example, the NPs can be administrated in blood circulation for monitoring cardiovascular system or in tumor for following drug delivery.

According to the present invention, a method for in vitro fluorescent detection of a biomolecular marker of diseases in a sample, with amplification due to nanoparticle antenna effect, comprises the step of:
- contacting the dye-loaded fluorescent polymeric nanoparticles of the present invention with said sample,
- illuminating at power densities equivalent to ambient sunlight conditions, preferably at an power density from 1 to 30 mW/cm$^2$
- and detecting the donor and amplified acceptor fluorescence emission.

In the presence of a one or several biomolecules (biomarkers), donor-acceptor energy transfer will be modified, resulting in an amplified response of the large ensemble of donors within the nano-antenna. For example, when one biomolecule disrupts donor-acceptor energy transfer, the emission of >100 donors in the nanoparticle would increase, whereas the amplified emission of the acceptor would decrease.

BRIEF DESCRIPTION OF THE DRAWINGS

The present invention is further illustrated by following figures and examples.

FIGURES

Figure 1:
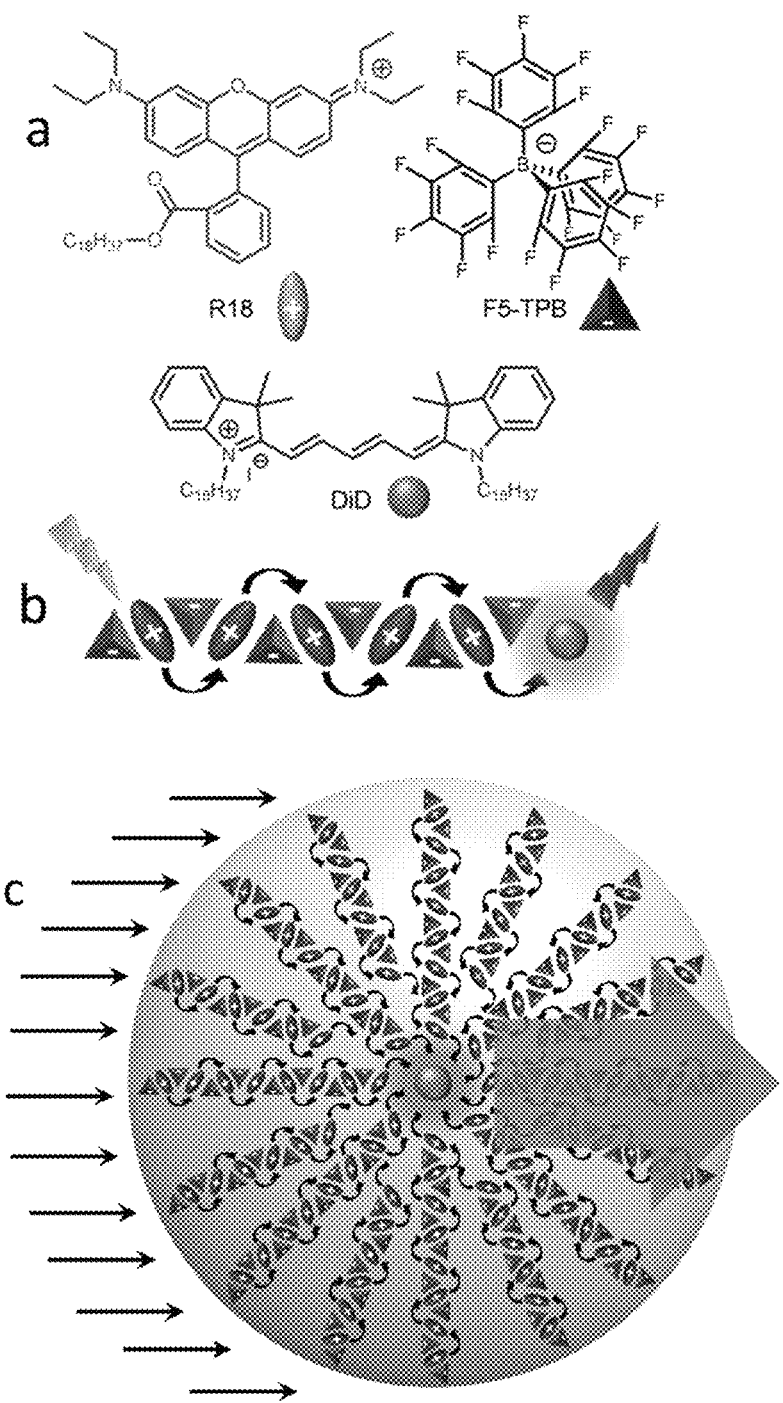

FIG. 1 shows the concept of a nanoparticle of the invention. (a) Chemical structures of the donor dye rhodamine B octadecyl ester (R18) and its counterion tetrakis(pentafluorophenyl)borate (F5-TPB) and of the acceptor dye cyanine 5 DiD. (b) Short-range ordering of R18 cations (represented by an oval) by the F5-TPB counterion (represented by a triangle) inside the PMMA-MA matrix prevents dye aggregation and leads to short interfluorophore distance and ultrafast EET with subsequent FRET to a single acceptor molecule (represented by a circle). (c) Schematic presentation of the giant light harvesting nano-antenna concept inside polymer NPs.

FIG. 2 shows spectroscopic characterization of the nanoparticles of the invention. (a) Steady-state fluorescence anisotropy and quantum yield of the encapsulated energy donors (R18/F5-TPB) as a function of their loading in PMMA-MA NPs (44 nm by TEM). (b) Schematic presentation of fluorescence anisotropy loss due to EET within randomly oriented fluorophores (c) Anisotropy decay measured at 580 nm with a 60-fs probe beam for NPs loaded at 1 and 30 wt % of donor dyes. (d) Emission spectra of FRET NPs loaded with different amounts of the acceptor dye (DiD) while keeping the same amount of the donor (30 wt %). The emission intensity was normalized to the same absorbance of the donor. (e) Experimental FRET efficiency for NPs of the invention with varied donor but constant acceptor (0.004 wt %) concentration and the calculated one assuming no EET within donor dyes. (f) Amplification factor of the acceptor emission (antenna effect) measured from the excitation spectra, its estimated values based on the observed FRET efficiency and theoretical estimation assuming no EET. Error bars in (a, e, f) represent the standard error of the mean (s.e.m., n=3).

Figure 3:
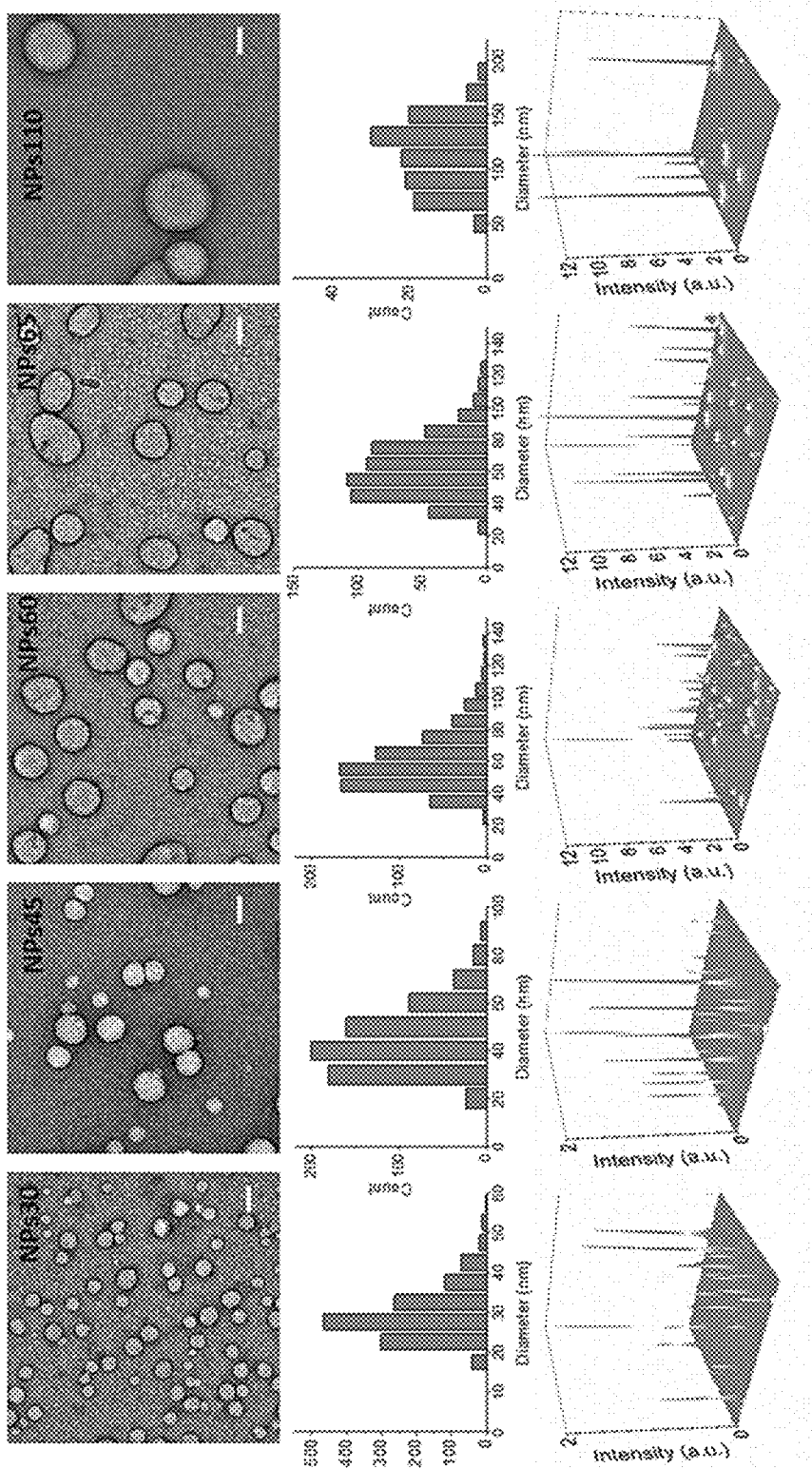

FIG. 3 shows size and brightness of individual nanoparticles of the invention. (a) TEM images and size histograms of NPs containing 30 wt % R18/F5-TPB prepared with different pH of buffer. Scale bar is 50 nm (b) 3D represen-
tation of wide-field fluorescence microscopy images of these NPs under illumination of a 532 nm laser with power 0.1 W/cm$^2$.

Figure 4:
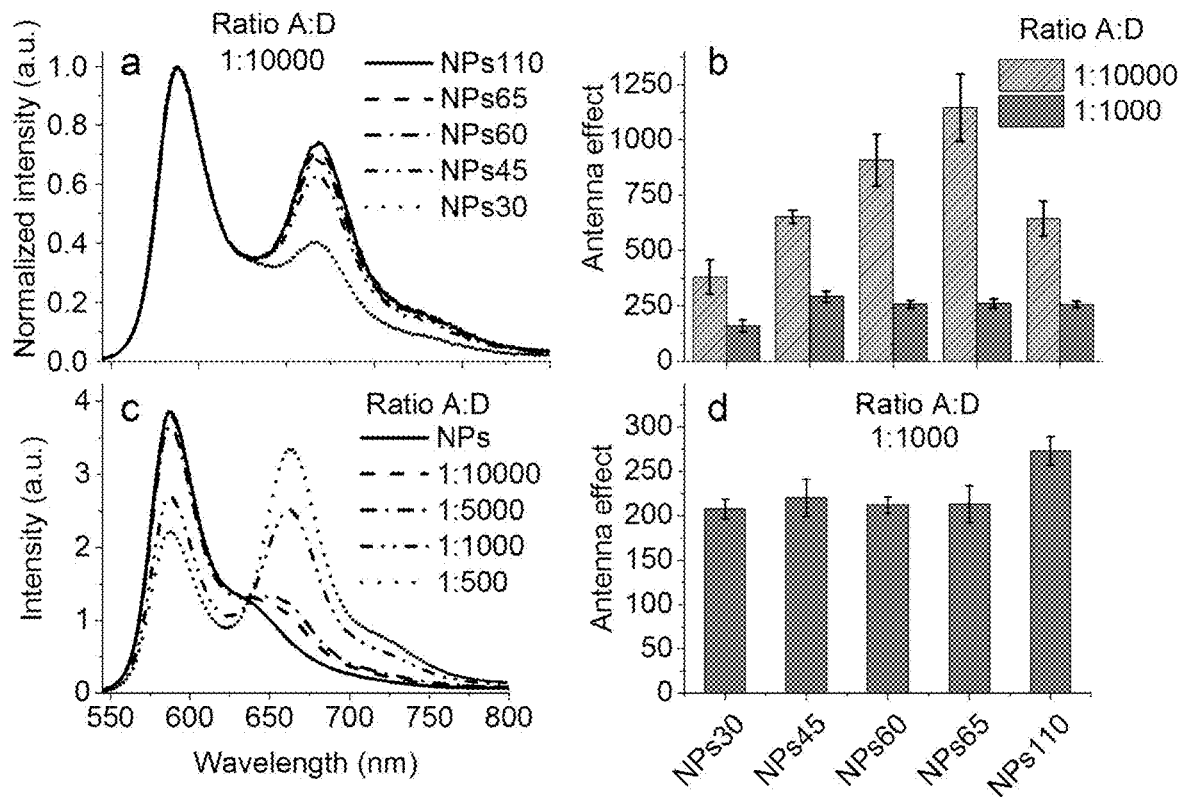

FIG. 4 shows effect of size of the nanoparticles of the invention on their performance. Fluorescence spectra (a), FRET efficiency and antenna effect (b) of PMMA-MA FRET NPs of different size loaded with 30 wt % of R18/F5-TPB and DiD. Donor/Acceptor ratios were 1000:1 or 10000:1. Error bars represent the standard error of the mean (n=3). Sample marked "No EET" represents theoretical calculations in the absence of exciton diffusion within donor dyes. (c) Spectra of NPs45 loaded with 30 wt % of R18/F5-TPB upon addition of acceptor molecule Cy5C2. (d) Amplification of acceptor emission (antenna effect) of Cy5C2 adsorbed on the surface of NPs of different sizes loaded with 30 wt % of donor at an acceptor concentration corresponding to a donor/acceptor ratio of 1000:1. Error bars represent s.e.m. (n=3).

FIG. 5 shows single-particle evaluation of performance of the nanoparticles of the invention. (a) Wide-field fluorescence microscopy images of NPs. Right panel represents images of NPs60 containing 30 wt % R18/F5-TPB without acceptor and left ones are those with ~1.5 Cy5 (DiD) acceptors per NP. The illumination at 532 nm was set to a laser power density of 1 W/cm$^2$. Both channels are represented at the same intensity scale. (b) 3D representation of wide-field TIRF images of acceptor emission from NPs60 nano-antenna containing ~1.5 Cy5 acceptors per NP under the illumination at 532 nm with laser power density of 0.1 W/cm$^2$, under the direct excitation of acceptor at 642 nm with laser power density of 100 W/cm$^2$ and of QD655 under illumination at 532 nm with laser power 0.1 W/cm$^2$. In all cases integration time was 30.53 ms. (c) Amplification factor of acceptor emission calculated by eq. 1 for antennas of different size with 1-2 acceptors per NP. (d) Representative single particle trace excited at 532 nm with a power density of 1 mW/cm$^2$. (e) Scheme of experimental setup using excitation by external light source that mimics direct sunlight. (f) Donor and acceptor channels of single particle microscopy under sunlight excitation mimics using NPs60 nano-antennas containing ~1.5 Cy5 per NP before and after 5 min illumination, and of NPs without acceptor under the same conditions. (g) Single particle traces at the acceptor channel for the nano-antennas without and with Cy5 acceptor.

Figure 6:
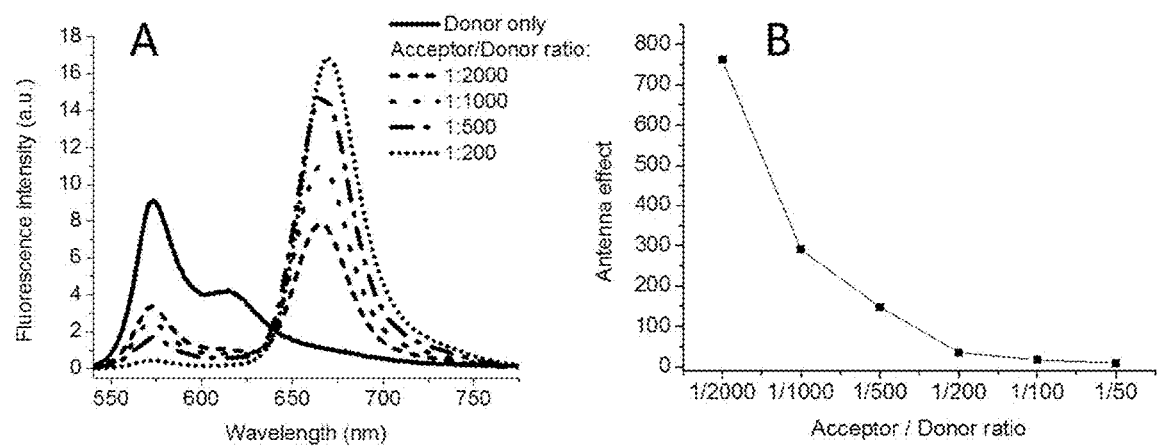

FIG. 6(A) shows fluorescence spectra of PMMA nanoparticles containing ~50 wt % (with respect to the polymer) of DiI cyanine dye salt with F12-TPB counterion (energy donor) and DiD cyanine dye salt with F12-TPB counterion (energy acceptor) at different acceptor/donor ratios. Excitation wavelength was 520 nm.

FIG. 6(B) shows antenna effect calculated from the excitation spectra of PMMA-MA nanoparticles containing ~50 wt % (with respect to the polymer) of DiI cyanine dye salt with F12-TPB counterion (energy donor) and DiD cyanine dye salt with F12-TPB counterion (energy acceptor) at different acceptor/donor ratios.

DETAILED DESCRIPTION

Materials and Methods

Materials. Poly (methyl methacrylate-co-methacrylic acid) (PMMA-MA, 1.3% methacrylic acid, Mn ~15000, Mw ~34000), acetonitrile (anhydrous, 99.8%), rhodamine B octadecyl ester perchlorate (>98.0%), lithium tetrakis (pentafluorophenyl)borate ethyl etherate were purchased from Sigma-Aldrich. DiD oil (1,1'-Dioctadecyl-3,3,3',3'-Tetramethylindodicarbocyanine Perchlorate) (Cy5) was purchased from Life-Technologies. Sodium phosphate monobasic (>99.0%, Sigma-Aldrich) and sodium phosphate dibasic dihydrate (>99.0%, Sigma-Aldrich) were used to prepare 20 mM phosphate buffers at pH 5.8-9.0. Milli-Q water (Millipore) was used in all experiments.

Synthesis. Rhodamine B Octadecyl Ester Tetrakis(pentafluorophenyl)borate (R18/F5) was synthesized by ion exchange and purified by column chromatography as described by Holzmeister et al. (Holzmeister, P.; Acuna, G. P.; Grohmann, D.; Tinnefeld, P. *Chemical Society Reviews* 2014, 43, (4), 1014-1028). 1,1'-Diethyl-3,3,3',3'-tetramethylindodicarbocyanine iodide (Cy5-C2) was synthesized as described by Pisoni et al. (Pisoni D. S.; Todeschini L.; Borges A. C. A.; Petzhold C. L.; Rodembusch F. S.; Campo L. F.; J. Org. Chem. 2014, 79, 5511.)

Nanoparticle Preparation. Stock solutions of the polymer in acetonitrile were prepared at a concentration 2 mg mL$^{-1}$ containing different amount of R18/F5-TPB (0.1 to 30 wt % relative to the polymer). 50 µL of the polymer solutions were then added quickly using a micropipette and under shaking (Thermomixer comfort, Eppendorf, 1000 rpm) to 450 µL of 20 mM phosphate at 21° C. The particle solution was then quickly diluted 5-fold with the phosphate buffer 20 mM, pH7.4. For preparation of FRET nanoparticles, different concentrations of DiD (from 0.001 wt % to 0.04 wt % relative to the polymer) were added to the acetonitrile solution of polymer containing desired concentration of R18/F5-TPB, and the particles were prepared as described above. Preparation of NPs of different size was achieved by varying the pH of phosphate buffer at the first dilution.

Nanoparticle characterization. Measurements for the determination of the size of nanoparticles were performed on a Zetasizer Nano ZSP (Malvern Instruments S.A.). The mean value of the diameter of the size distribution per volume was used for analysis. Absorption spectra were recorded on a Cary 4000 scan UV-visible spectrophotometer (Varian), excitation and emission spectra were recorded on a Fluoro-Max-4 spectrofluorometer (Horiba Jobin Yvon) equipped with a thermostated cell compartment. For standard recording of fluorescence spectra, the excitation wavelength was set to 530 nm. The fluorescence spectra were corrected for detector response and lamp fluctuations. To calculate FRET efficiency based on fluorescence spectra, a classical equation was used:

$$E_{FRET} = 1 - \frac{I_{D-A}}{I_D},$$

where $I_D$ is the integral donor intensity and $I_{D-A}$ the integral intensity of the donor in the presence of the acceptor. Measurement of fluorescence anisotropy was performed at 20° C. with a Fluorolog spectrofluorometer (Horiba Jobin Yvon). Excitation wavelength was set to 530 nm and detection to 585 nm. Each measurement of the anisotropy value corresponds to an average over 10 subsequent measurements of 0.1 s each. The anisotropy value (r) was expressed as $r=(I_{\parallel}-I_{\perp})/(I_{\parallel}+2I_{\perp})$. To measure the anisotropy value of Cy5-C2 the excitation wavelength was 620 nm and emission wavelength 655 nm. For standard recording of excitation spectra, the emission wavelength was set to 700 nm. These spectra were corrected for the lamp intensity. Amplification factor of the acceptor emission (antenna effect, AE) was then expressed as the ratio of the maximal excitation intensity of the donor to that of the acceptor with correction from the emission of the donor dyes at 700 nm:

$$AE = \frac{I^{ex}_{D-FRET} - I^{ex}_D * f}{I^{ex}_{A-FRET}}$$

Where $I_{D-FRET}^{ex}$ and $I_{A-FRET}^{ex}$ are the maximal excitation intensities of donor and acceptor in FRET NPs, respectively; $I_D^{ex}$ and $I_A^{ex}$ are the excitation intensities at the wavelengths of excitation maximum of donor and acceptor in NPs without acceptors, respectively; f is the correction factor calculated as the ratio of maximum emission intensity of donor for FRET NPs to that for NPs without acceptor dyes:

$$\left( f = \frac{I^{em}_{D-FRET}}{I^{em}_D} \right).$$

The value of the antenna effect was also estimated based on the FRET efficiency using the following equation: AE=$(n_D \times \varepsilon_D \times E)/(n_A \times \varepsilon_A)$, where $n_D$ and $n_A$ are the numbers of donors and acceptors, respectively, per particle, $\varepsilon_D$ and $\varepsilon_A$ are the extinction coefficients of donors and acceptors, respectively, and E is the FRET efficiency. QYs of NPs were calculated using Rhodamine 101 (QY=1) in ethanol as a reference with an absorbance of 0.01 at 530 nm (Sauer, M.; Hofkens, J.; Enderlein, J., *Handbook of Fluorescence Spectroscopy and Imaging: From Ensemble to Single Molecules.* Wiley-VCH: 2011). QY of an acceptor molecule DiD in PMMA-MA matrix was calculated for the concentration 0.02 wt % using DiD in methanol (QY=0.33) as a reference (Magidson, V.; Khodjakov, A., Chapter 23-Circumventing Photodamage in Live-Cell Microscopy. In *Methods in Cell Biology*, Greenfield, S.; David, E. W., Eds. Academic Press: 2013; Vol. Volume 114, pp 545-560).

Time-resolved anisotropy. For the time-resolved anisotropy measurements, we used an amplified Ti: sapphire laser that produces ultrashort pulses (100 fs) at a repetition rate of 100 kHz. 60 fs linearly polarized pulses centered at 520 nm ($\Delta\lambda$=12 nm) were obtained by means of an optical parametric amplifier (OPA). The pump's power density was around 120 W cm$^{-2}$ for all the measurements. Ultrashort continuum probe pulses were generated in a sapphire crystal (500-800 nm). The normalized differential transmission of a 60 fs ( $$\left(\frac{\Delta T}{T}\right) = \frac{I_t^p - I_t^0 - I_{fl}^p}{I_t^0}$$

where $I_t^p$ and $I_t^0$ are the intensities of the transmitted probe with and without pump and $I_{fl}^p$ is the fluorescence intensity generated by the pump) linearly polarized probe (parallel or perpendicular to the pump polarization) centered around 580 nm ($\Delta\lambda$=13 nm) was measured as a function of the pump-probe delay by using a monochromator coupled to a liquid nitrogen cooled CCD (Princeton Instrument). The anisotropy decay was calculated using the following relation $$\frac{\left(\frac{\Delta T_{\parallel}}{T_{\parallel}} - \frac{\Delta T_{\perp}}{T_{\perp}}\right)}{\left(\frac{\Delta T_{\parallel}}{T_{\parallel}} + 2\frac{\Delta T_{\perp}}{T_{\perp}}\right)},$$

where $\parallel$ and $\perp$ denotes for a probe beam with a linear polarization parallel and perpendicular with respect to the linear polarization of the pump beam. The decay curves were fitted with a bi-exponential function and the analysis took into account the laser pulse duration.

Transmission electron microscopy (TEM). Five microliters of the particles solution were deposited onto carbon-coated copper-rhodium electron microscopy grids that were used either as obtained or following an air or amylamine glow-discharge. The grids were then treated for 1 min with a 2% uranyl acetate solution for staining. They were then observed with a Philips CM120 transmission electron microscope equipped with a LaB6 filament and operating at 100 kV. Areas covered with nanoparticles of interest were recorded at different magnifications on a Peltier cooled CCD camera (Model 794, Gatan, Pleasanton, Calif.). Image analysis was performed using the Fiji software.

Fluorescence Microscopy. For single particle fluorescence microscopy measurements, the NPs were immobilized on glass surfaces on which a polyethylenimine (PEI) layer was initially adsorbed. The solutions of NPs were diluted 5000, 2000, 1000 and 500 times for NPs30, NPs45, NPs60, NPs65 and NPs110 correspondingly. 400 μL of these solutions per $cm^2$ were then brought in contact with the PEI covered glass for 15 min, followed by extensive rinsing with Milli-Q-water. The surfaces were left in Milli-Q water during microscopy.

Single particle measurements were performed in the TIRF (Total Internal Reflection Fluorescence) mode on a home-made wide-field setup based on an Olympus IX-71 inverted microscope with a high-numerical aperture (NA) TIRF objective (Apo TIRF 100×, oil, NA 1.49, Olympus). A 532 nm diode laser (Cobolt Samba 100) and a 642 nm diode laser (Spectra-Physics Excelsior 635) were used to excite the samples. The 532 nm laser intensity was set to 1 mW/$cm^2$-100 mW/$cm^2$ by using a polarizer and a half-wave plate (532 nm). For direct excitation of acceptor Cy5, the 642 nm laser was used with intensity 0.1 kW/$cm^2$. The fluorescence signal was recorded with an EMCCD (ImagEM Hamamatsu) (0.106 μm pixel size) using an open source Micro-Manager software. The exposure time was set to 30.53 msec per image frame. To enable two channel images W-VIEW GEMINI image splitting optics were used with the following filter set: dichroic 640 nm (Semrock FF640-FDi01-25×36), bandpass filters 593±20 nm(Semrock FF01-593/40-25) and 685±20 nm (Semrock FF02-685/40-25)) were used to image R18/F5-TPB and Cy5, respectively. Single particle analysis was performed using the Fiji software: particle locations were detected through a Fiji routine applied to a projection (maximum intensity) of 1000 frames. After the automatic background subtraction, the mean intensities of circular regions of interest with a diameter of 8 pixels around the found particle locations were then measured. At least three image sequences (245 pixel×245 pixel) per condition were analyzed with, on average, 500-700 particles per sample.

Microscopy mimicking ambient sunlight excitation. The sunlight power density (24 mW $cm^{-2}$) was recorded at midday on 19 Oct. 2016, Strasbourg region, using Handheld Laser Power Meter, 1917-R and Semrock band-pass filter 527 nm (50 nm bandwidth). The artificial white light mimicking sunlight was provided by a Cold light source from Zeiss, type KL 1500 LCD. The sample was illuminated from the top ~2 cm from the divergent light source output through the same 527-nm filter, which corresponded to 15 mW $cm^{-2}$ power density at the sample. Single-molecule imaging was done using Nikon Ti-E inverted microscope using CFI Plan Apo 20× air (NA=0.75) and CFI Plan Apo 60× oil (NA=1.4) objectives and Hamamatsu Orca Flash 4 camera. Donor channel was recorded through a 600-nm band-pass filter (50 nm bandwidth, Semrock), while the acceptor channel used 647-nm long-pass filter (Semrock). Data were recorded and analyzed using NIS Elements and Fiji software, respectively.

Result

Spectroscopic Characterization of the NPs of the Invention

According to the theory, when the energy migrates within dyes randomly distributed inside a rigid polymer matrix, the fluorescence anisotropy should decrease (FIG. 2b). The results of FIG. 2a show that, as expected, an increase in the dye loading produces a fast drop in the fluorescence anisotropy values. By the way, the fluorescence quantum yields (QY) of the obtained NPs decreased with the donor loading but remained remarkably high (~30%) even at 30 wt % loading (FIG. 2a). This result corroborates with relatively small changes in the absorption spectra, where the short-wavelength shoulder, an indicator of donor aggregation, showed minimal increase. Moreover, the emission spectra of NPs of the invention displays only a small red shift without broadening. At 30 wt % loading the average distance between encapsulated dyes should be ~1 nm, which is far below the Förster radius of homo-FRET transfer for R18/F5-TPB at this loading (4.6 nm). Therefore, an efficient EET could take place, explaining this loss in the anisotropy. To understand better the EET process, femtosecond anisotropy decay studies are performed by using a pump-probe technique. For low dye loading (1 wt % of R18/F5-TPB), the anisotropy remained stable during the first 10 ps, indicating that EET in this system should be very slow (FIG. 2c). In sharp contrast, at high dye loading (30 wt %) the anisotropy decayed to zero already within 1 ps (FIG. 2c). The bi-exponential fit revealed 30 fs (45%) and 600 fs (55%) components, the former being limited by the resolution of the used setup (60 fs pulse width). This means that the EET process is exceptionally fast and thus can involve thousands of dyes (between $2.7 \times 10^3$ and $5.3 \times 10^4$) within their emission lifetime (~1.6 ns).

Further, a FRET acceptor is introduced into the NPs by nano-precipitating polymer together with donors and accepter in phosphate buffer. The chosen acceptor in this experience is the lipophilic cyanine 5 derivative DiD. It is a perfect energy acceptor for rhodamine B with very good spectral overlap, and its two hydrophobic octadecyl chains should ensure efficient encapsulation inside polymer matrix. Being encapsulated at 0.02 wt %, DiD displayed a high fluorescence quantum yield of 77±4%, so that the nanoparticle of the invention is tested on a highly emissive acceptor. For NPs containing 30 wt % of donor, an increase in the acceptor concentration resulted in a rapid growth of acceptor emission, accompanied by a drop of the donor emission, indicating a FRET process (FIG. 2d). Remarkably, efficient FRET (28±5%) is already observed for 0.004 wt % of the acceptor (with respect to the mass of the polymer), which corresponds to 1.2 acceptors per 44-nm particle. According to Poisson distribution this acceptor loading ensures that >67% of NPs contain at least one acceptor. Thus, in these NPs a single acceptor could produce FRET from ~5900 donors through distance of >20 nm (NPs radius) that is much larger than the Förster radius.

To understand better the role of exciton diffusion in this efficient FRET process, NPs are prepared with a constant concentration of the acceptor (0.004 wt %) and varied the concentration of the donor (0.1-30 wt %). Theoretical prediction, assuming no donor-donor communication (no EET), suggested negligibly low FRET efficiency (4-6%) for 0.004 wt % acceptor independently from the donor loading (FIG.

2e). By contrast, the results of the invention show that the increase in the donor loading produces a significant growth in the FRET efficiency (FIG. 2e) and an increase in the acceptor relative intensity. Together with fluorescence anisotropy data, this efficient FRET is clearly a result of fast EET that delivers energy from thousands of donors to a single acceptor (FIG. 2a-c).

Owing to the efficient FRET, NPs of the invention behave like light-harvesting nano-antenna. To quantify the antenna effect (AE), the excitation spectra of the donor and acceptor at the emission wavelength of the acceptor (700 nm) are recorded. AE is measured as the ratio of the maximal excitation intensity of the donor to that of the acceptor with correction from the emission of the donor dyes in the acceptor channel, as described in Materials and Methods.

At low loading of the donor, no antenna effect was observed (AE~1), whereas at higher donor loadings, AE increased rapidly reaching 560 for 44-nm NPs at 30 wt % (FIG. 2f). These values correlated well with the antenna effect calculated as AE=(nD$\epsilon$DE)/(nA$\epsilon$A), where nD and nA are the numbers of donors and acceptors, respectively, per particle, $\epsilon$D and $\epsilon$A are the extinction coefficients of donors and acceptors, respectively, and E is the FRET efficiency (FIG. 2e). By contrast, theoretical estimations assuming no EET gave AE values much below the experimental ones (3-6 fold lower), emphasizing the importance of the communication within donor dyes for obtaining an efficient antenna.

Effect of the Size of the Nanoparticles on Their Performance

The influence of the size of 30 wt % dye-loaded NPs on the nanoparticles performance is further investigated. Due to the strong effect of polymer charge on the size of obtained NPs, the pH of the phosphate buffer used in nanoprecipitation are varied, which could change the protonation state of the carboxylate in PMMA-MA polymer. Based on DLS measurements, a decrease in pH from 9.0 and 5.8 produces an increase in NP size from 30 to 230 nm, while preserving a good polydispersity (Table 2). TEM confirmed the increase in NPs size with decrease in pH of buffer, but revealed that the sizes of NPs were smaller, in the range of 30-67 nm for pH range from 9.0 to 6.5. However, for pH 5.8 aggregates of >100 nm size are observed (FIG. 3a).

Independently of the size, the QY of 30 wt % dye-loaded NPs remained high (0.27-0.31, Table 2). Moreover, according to wide-field fluorescence microscopy of NPs immobilized on the surface, the single particle brightness increased with size (FIG. 3b), so that the largest NPs (NPs110) were 31 times as bright as the smallest ones (NPs30) (Table 2). The experimental brightness correlates well with the estimations based on QY and the size of NPs measured by TEM (Table 2). Finally, the anisotropy values are close to zero for all particles sizes (Table 2), indicating that EET is efficient in all these systems.

Using different pH of phosphate buffer, nanoparticles of different size containing 30 wt % of R18/F5-TPB donors with varied amount of acceptor corresponding to donor/acceptor ratio 1000 and 10000 (0.02 and 0.002 wt %, respectively) are prepared. For both ratios, an increase in the NP size increases the contribution of the acceptor emission (FIG. 4a) and the FRET efficiency (FIG. 4b). Thus, for the same donor/acceptor ratio, the larger antennas transfer the energy more efficiently to the acceptor. The antenna effect also increases with NP size, especially for NPs with donor/acceptor ratio of 10000 (FIG. 4b). Remarkably, for NPs60 and NPs65 (containing 1.3 and 1.7 acceptors per NP, respectively) the antenna effect reached 910±120 and 1150±150, respectively (FIG. 4b). It is also verified whether the nano-antennas of the invention can amplify fluorescence of acceptor dye directly at the particle surface, using a less hydrophobic analogue of DiD, Cy5-C2. According to fluorescence anisotropy data, Cy5-C2 at 15 nM concentration binds the NPs of the invention at the used concentrations (0.04 g/L). Being bound to NPs it exhibited good quantum yield (28±4%). In case of 45 nm NPs loaded at 30 wt % with R8/F5-TPB, a strong FRET with nearly equal intensity of acceptor and donor bands was observed for a donor-acceptor ratio of 1000 (FIG. 4c). Remarkably, based on the excitation spectra the antenna effect for NPs of different sizes was systematically above 200 (FIG. 4d). Thus, nano-antennas of the invention can strongly amplify the acceptor emission also at their surface, although the antenna effect is weaker than for the acceptor inside NPs. The amplification of the acceptor emission at the surface is of key importance for obtaining FRET-based fluorescent probes for detection of biomolecules.

Single-Particle Evaluation of Nanoparticles Performance

To carry out this evaluation, the nanoparticles of invention are immobilized on the glass surface and imaged them by wide-field TIRF microscopy. The control NPs without acceptors appear as bright spots at the donor channel and as dim spots at the acceptor channel. In the presence of ~1.3 acceptors/nanoparticle, the emission in the acceptor channel

TABLE 2

Hydrodynamic diameter and spectroscopic properties of PMMA-MA NPs encapsulating 30 wt % of R18/F5-TPB prepared at varied pH.

| Sample | pH[a] | Size, DLS (nm)[b] | Size, TEM (nm)[c] | QY[e] | Anisotropy | Donors/NP[f] | SPB[g] estim. | SPB[h] exp. |
|---|---|---|---|---|---|---|---|---|
| NPs30 | 9.0 | 36 ± 1 | 29 ± 1 | 0.31 ± 0.04 | 0.001 | 1700 | 1 | 1 |
| NPs45 | 7.4 | 67 ± 2 | 44 ± 2 | 0.30 ± 0.03 | 0.0028 | 5900 | 3 | 5 |
| NPs60 | 6.7 | 105 ± 5 | 58 ± 2 | 0.28 ± 0.03 | 0.0025 | 13000 | 7 | 12 |
| NPs67 | 6.5 | 144 ± 6 | 63 ± 4 | 0.27 ± 0.03 | 0.0024 | 17000 | 9 | 20 |
| NPs107 | 5.8 | 231 ± 16 | 113 ± 6 | 0.29 ± 0.03 | 0.0029 | 99000 | 54 | 31 |

[a]After preparation, NPs were diluted in pH 7.4 buffer.
[b]Statistics by volume was used in DLS measurements (error is s.e.m., n = 5 PDI (polydispersity index) values were 0.1-0.2 for all NPs.
[c]Mean and standard error of the mean (s.e.m.) are calculated from 80-500 NPs in two independent preparations.
[d]Mean ± s.e.m. fluorescence lifetime (n = 3).
[e]Quantum yield ± s.e.m. of NPs without acceptor molecules (n = 5).
[f]Estimation is based on NPs size measured by TEM.
[g]Estimated single particle brightness normalized to NPs30 based on QY and size of NPs measured by TEM.
[h]Normalized experimental single particle brightness of NPs under illumination of a 532-nm laser with 0.1 W cm$^{-2}$ power density.

becomes comparable or brighter than that in the donor channel (FIG. 5a). This result shows that inside the nanoparticles, the emission of 1-2 acceptors is comparable to the emission of thousands of donor dyes.

To quantify the amplification of acceptor emission under the microscope, the acceptor intensity under excitation through FRET at 532 nm is compared to that obtained by direct excitation with a 642 nm laser. Remarkably, to obtain similar acceptor intensities, the excitation through nanoparticles NPs60 at 532 nm required ~1000-fold lower laser power than direct excitation of the acceptor at 642 nm (FIG. 5b). The amplification factor (AF) of acceptor emission at the single particle level was determined as:

$$AF = \frac{I_A^{532\,nm}}{I_A^{642\,nm}} \times \frac{P^{642\,nm}}{P^{532\,nm}} \quad (1)$$

where $I_A^{532\,nm}$ and $I_A^{642\,nm}$ are the mean intensities of acceptors under excitation at 532 and 642 nm, respectively, and $P^{532\,nm}$ and $p^{642\,nm}$ are laser powers at the corresponding wavelengths. Using equation (1), it is found that the amplification factor increased with the particle size (FIG. 5c). For NPs60, we obtained a ~1040±100-fold amplification factor, which is in good agreement with the antenna effect measured from the excitation spectra. Owing to this giant amplification factor, the brightness of 1-2 acceptors inside NPs60 is 25-times higher than that of a QD655 excited at 532 nm with the same power (FIG. 5b). This is an exceptional performance of single Cy5 dyes, taking into account that the extinction coefficient of QD655 at 532 nm is $2.4 \times 10^6$ $M^{-1}cm^{-1}$ (data from the provider) and QY is close to unity.

Finally, using the nanoparticle of invention NPs60, we can observe single molecule events, such as one-step bleaching of the Cy5 (DiD) acceptor at extremely low laser powers of 1 mW/cm² (FIG. 5d), which is accompanied by one step growth of the donor emission. This opposite behavior of donor and acceptor is typically observed in single molecule FRET measurements using one donor and acceptor dyes, but here FRET takes place between 15000 donors and 1-2 acceptors. Moreover, previous reports on single-molecule detection were systematically based on light power densities of 10-5000 W/cm². In the present invention, similar single molecule traces are observed at 1-10 mW/cm², reaching the values of the ambient sunlight.

Therefore, whether the NPs of the invention enable detection of single molecules using a simple microscopy setup is tested by the excitation provided by directly shining light on the sample at powers equivalent to sunlight. The measured power of direct sunlight (at midday, 19 Oct. 2016, Strasbourg) through the excitation filter 527/50 nm was 24 mW cm⁻². In the used setup, an artificial white light source providing 15 mW cm⁻² through the same filter is used. The fluorescence of immobilized NPs60 nanoparticles with ~1.5 Cy5 dyes is collected using either 20× air or 60× oil immersion objective and detected using sCMOS camera (FIG. 5e). These NPs displayed significant acceptor emission in contrast to control NPs without acceptor (FIG. 5f). Moreover, after 5-min illumination with an artificial light source, the former NPs lost the acceptor emission, probably due to acceptor bleaching, and became similar to the control NPs. Strikingly, using 20× air objective, it is able to record in the acceptor channel one-step bleaching events, corresponding to single Cy5 dye molecules (FIG. 5g). By contrast, the control NPs display much lower intensity at the acceptor channel without abrupt bleaching steps.

Cyanine dyes were also tested as energy donors in PMMA-based nanoparticles of ~45 nm diameter. Following the same protocol as for R18/F5-TPB, we prepared PMMA-MA NPs containing ~50 wt % with respect to polymer mass (~130 mmol/kg of total particle mass) of DiI cyanine dye salt with F12-TPB counterion as energy donor. DiD salt with F12-TPB was used as energy acceptor co-encapsulated with the energy donor at different molar ratios. It was found that FRET between DiI and DiD was efficient even at very low acceptor/donor ratio 1/2000 (FIG. 6A), indicating very efficient light-harvesting processes from donors to a single acceptor. Based on the excitation spectra, the measured antenna effect increased with decrease in the acceptor/donor ratio, reaching values close to 800 (FIG. 6B). The result is similar to that observed for R18/F5-TPB as energy donor, which shows that cyanine dyes can also be used to preparation of light-harvesting nanoantenna.

The invention claimed is:

1. A dye-loaded fluorescent polymeric nanoparticle as nano-antenna, comprising:
   a) a polymer chosen from:
      a polymethacrylate or its derivative;
      a polystyrene or its derivative;
      an aliphatic polyester or its derivative; or
      a copolymer of aforementioned polymers with polyethylene glycol (PEG) or with charged monomers;
   b) an energy donor, which content is from 5 to 50% by weight of the polymer; and
   c) an energy acceptor, which content from 0.001 to 0.04% by weight of the polymer;

said polymer forming a matrix in which from 1000 to 50000 of said energy donor molecules are encapsulated per nanoparticle, wherein the energy donor is a salt of a donor dye with bulky fluorinated anions, said donor dye being chosen from:
(i) a rhodamine derivative represented by formula (I)

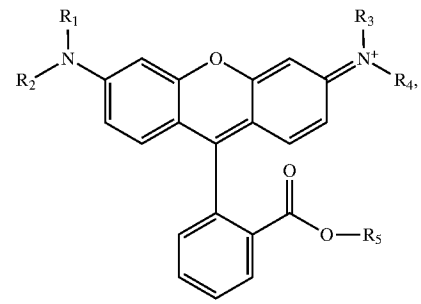

in which:
R1, R2, R3 and R4 are identical or different and each represent a hydrogen or a (C1-C8) alkyl group;
R5 is a (C1-C24) alkyl; or
(ii) a cyanine derivative represented by formula (II)

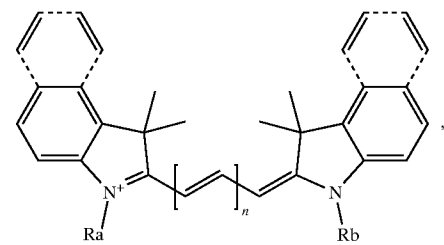

in which:
n is a integer chosen from 1, 2 or 3;
Ra and Rb are identical or different and each represent a (C1-C24) alkyl group; and
wherein the energy acceptor is a salt of another cyanine derivative of formula (II) defined above with a counterion, said energy donor and said energy acceptor being different.

2. The dye-loaded fluorescent polymeric nanoparticle according to claim 1, wherein the polymer is chosen from polycaprolactone, poly(lactic acid), poly(glycolic acid), poly(Lactide-co-Glycolide), Poly(methyl methacrylate), poly(methyl methacrylate-co-methacrylic acid), and poly (Lactide-co-Glycolide-co-PEG).

3. The dye-loaded fluorescent polymeric nanoparticle according to claim 1, wherein the content of energy donor is from 50 to 700 mmol/kg with respect to the total mass of the nanoparticles.

4. The dye-loaded fluorescent polymeric nanoparticle according to claim 1, wherein the bulky fluorinated anion is chosen from tetrakis(pentafluorophenyl)borate (F5-TPB), tetrakis[3,5-bis-(trifluoromethyl)phenyl]borate (F6-TPB), tetrakis[3,5-bis-(1,1,1,3,3,3-hexafluoro-2-methoxy-2-propyl)phenyl]borate (F12-TPB), and tetrakis[perfluoro-tert-butoxy]aluminate (F9-Al).

5. The dye-loaded fluorescent polymeric nanoparticle according to claim 1, wherein the counterion of the energy acceptor is an inorganic anion chosen from chloride, bromide, iodide, perchlorate, sulfonate, nitrate, tosylate, or an organic anion chosen from tetrakis(pentafluorophenyl)borate (F5-TPB), tetrakis[3,5-bis-(trifluoromethyl)phenyl]borate (F6-TPB), tetrakis[3,5-bis-(1,1,1,3,3,3-hexafluoro-2-methoxy-2-propyl)phenyl]borate (F12-TPB), and tetrakis [perfluoro-tert-butoxy]aluminate (F9-Al).

6. The dye-loaded fluorescent polymeric nanoparticle according to claim 1, wherein:
the energy donor is chosen from a salt of rhodamine B octadecyl ester, Cy3, Cy5, Cy3.5, or Cy5.5 with an above-mentioned bulky fluorinated anion; and
the energy acceptor is chosen from a salt of Cy5, Cy5.5, Cy7, Cy 7.5 with an above-mentioned anion;
said energy donor and said energy acceptor being different.

7. The dye-loaded fluorescent polymeric nanoparticle according to claim 6, wherein the energy donor and the energy acceptor in said nanoparticle
form a couple of energy donor/energy acceptor, which is chosen from below table:

| Donor/Acceptor couple: |
| --- |
| rhodamine B octadecyl ester salt/DiD salt |
| rhodamine B octadecyl ester salt/Cy5.5 salt |
| DiI salt/ DiD salt |
| DiI salt/Cy5.5 salt |
| DiI salt/Cy7 salt |
| DiD salt/Cy7 salt |
| Cy3.5 salt/Cy5.5 salt |
| Cy3.5 salt/Cy7.5 salt |
| Cy5.5 salt/Cy7.5 salt. |

8. The dye-loaded fluorescent polymeric nanoparticle according to claim 1, wherein the nanoparticle has a diameter of 10 nm to 150 nm.

9. The dye-loaded fluorescent polymeric nanoparticle according to claim 1, wherein the ratio between the energy acceptor and energy donor is from 1:100 to 1:50000.

10. The dye-loaded fluorescent polymeric nanoparticle according to claim 1, wherein the excitation power density of said fluorescent polymeric nanoparticle is from 1 to 1000 mW/cm2, at 530 nm with up to 50 nm bandwidth.

11. The dye-loaded fluorescent polymeric nanoparticle according to claim 1, wherein the energy acceptor is either encapsulated inside the matrix of polymer or linked to or adsorbed on the surface of polymer.

12. The dye-loaded fluorescent polymeric nanoparticle according to claim 1, wherein the surface of said nanoparticle is
modified through the adsorption of a polymeric or lipidic amphiphile
bearing at least one polyethylene glycol chain or zwitterionic groups, preferably poloxamers, polysorbates, and 1, 2-distearoyl-sn-glycero-3-phosphoethanolamine-Poly(ethylene glycol); or
covalently modified by polyethylene glycol or zwitterionic groups.

13. A method for producing a dye-loaded fluorescent polymeric nanoparticle according to claim 1, with an energy acceptor and an energy donor encapsulated inside the nanoparticle, comprising:
(i) preparing a water-miscible solvent solution of a polymer as defined in claim 1 containing;
a. from 0.001 to 0.04% by weight of the polymer of the polymer of an energy acceptor defined in claim 1; and
b. from 5 to 50% by weight of the polymer of an energy donor defined in claim 1; and
(ii) nanoprecipitating said water-miscible solvent solution of polymer in a basic, neutral or weakly acidic aqueous buffer to obtain said polymer based fluorescent nanoparticles.

14. A method for producing a dye-loaded fluorescent polymeric nanoparticles according to claim 1 with an energy acceptor absorbed at the nanoparticle surface and an energy donor encapsulated inside the nanoparticle, comprising:
(i) preparing a water-miscible solvent solution of polymer as defined in claim 1 at 0.1-5 mg/ml containing from 5 to 50% by weight of the polymer of an energy donor;
(ii) nanoprecipitating said water-miscible solvent solution of polymer in a basic, neutral or weakly acidic aqueous buffer to obtain a nanoparticle which encapsulates the energy donor; and
(iii) adding a water-miscible solvent solution of acceptor to above aqueous buffer containing nanoparticles to a final concentration from 0.001 to 0.04% by weight of the polymer.

15. A method for detecting single biomolecules in vitro or in vivo, the method comprising contacting a biomolecule in vitro or in vivo with the dye-loaded fluorescent polymeric nanoparticle of claim 1.

16. A method for in vitro fluorescent detection of a biomolecular marker of a disease in a sample, with amplification due to nanoparticle antenna effect, comprising the step of:
contacting the dye-loaded fluorescent polymeric nanoparticle according to claim 1 with said sample;
illuminating at power densities equivalent to ambient sunlight conditions; and
detecting the donor and amplified acceptor fluorescence emission.

* * * * *